(12) United States Patent
Molenda et al.

(10) Patent No.: US 9,616,012 B2
(45) Date of Patent: Apr. 11, 2017

(54) CONDITIONING COMPOSITION FOR HAIR

(75) Inventors: Michael Molenda, Frankfurt (DE); Ilka Tietjen, Ilvesheim (DE)

(73) Assignee: KAO Germany GmbH, Darmstadt (DE)

( * ) Notice: Subject to any disclaimer, the term of this patent is extended or adjusted under 35 U.S.C. 154(b) by 187 days.

(21) Appl. No.: 13/814,110

(22) PCT Filed: Aug. 1, 2011

(86) PCT No.: PCT/EP2011/063203
§ 371 (c)(1),
(2), (4) Date: Mar. 4, 2013

(87) PCT Pub. No.: WO2012/016943
PCT Pub. Date: Feb. 9, 2012

(65) Prior Publication Data
US 2013/0164244 A1    Jun. 27, 2013

(30) Foreign Application Priority Data
Aug. 5, 2010 (EP) .................................. 10008174

(51) Int. Cl.
*A61K 8/73* (2006.01)
*A61Q 5/12* (2006.01)
*A61Q 5/00* (2006.01)
*A61Q 5/02* (2006.01)

(52) U.S. Cl.
CPC ............... *A61K 8/73* (2013.01); *A61K 8/732* (2013.01); *A61Q 5/002* (2013.01); *A61Q 5/12* (2013.01); *A61K 2800/5922* (2013.01); *A61Q 5/02* (2013.01)

(58) Field of Classification Search
CPC . A61Q 5/12; A61Q 5/02; A61Q 5/002; A61K 8/732; A61K 8/73; A61K 2800/5922
See application file for complete search history.

(56) References Cited

U.S. PATENT DOCUMENTS

| 8,048,836 B2* | 11/2011 | Molenda et al. ............. 510/122 |
| 2004/0120914 A1* | 6/2004 | Decoster ................ A61K 8/416 424/70.12 |
| 2005/0198747 A1* | 9/2005 | Emmerling et al. ............. 8/406 |
| 2009/0257972 A1* | 10/2009 | Dieker ................... A61K 8/365 424/70.13 |

FOREIGN PATENT DOCUMENTS

| DE | EP 1779838 A1 * | 5/2007 | ............. A61K 8/416 |
| DE | EP 2196186 A1 * | 6/2010 | ............... A61K 8/39 |

OTHER PUBLICATIONS

Repair Shampoo L013-26B-306, drstraetmans (Jan. 2010), downloaded from https://web.archive.org/web/20100108021850/http://www.kinetiktech.com/formulations/hair/Repair_Shampoo_DS.pdf, Jul. 14, 2014.*
Personal Care Ingredients, "Symbiosis Harnessed for Agent," Personal Care Magazine (2008) accessed at http://www.personalcaremagazine.com/Print.aspx? Story=4306, downloaded Jul. 14, 2014.*
Kinetik, Product Guide pp. 1-27, downloaded from https://web.archive.org/web/20091014194806/http://www.kinetiktech.com/docs/product_list.pdf, available online Oct. 2009.*
"Introducing SYMBIO quat", drstraetmans, available on line 2009.*
"Color Saver Shampoo". drstraetmans, L013-24C-3088 available online Jan. 2010.*
Kinetik 2009 product catalogue, accessed at https://web.archive.org/web/20091014194806/http://www.kinetiktech.com/docs/product_list.pdf.*

* cited by examiner

*Primary Examiner* — Kortney L Klinkel
*Assistant Examiner* — Lisbeth C Robinson
(74) *Attorney, Agent, or Firm* — Norris McLaughlin & Marcus, P.A.

(57) ABSTRACT

The present invention is related to aqueous conditioning composition for hair comprising at least one cationic starch polymer and at least one additional cationic polymer selected from the ones with monosaccharide units. Conditioning composition of the present invention can be in the form of a shampoo, cleansing-conditioning composition, or in the form of a conditioner used after washing hair with cleansing compositions.

14 Claims, No Drawings

CONDITIONING COMPOSITION FOR HAIR

This application is a 371 application of PCT/EP2011/063203 filed Aug. 1, 2011, which claims foreign priority benefit under 35 U.S.C. §119 of European Application No. 10008174.4 filed Aug. 5, 2010.

The present invention is related to aqueous conditioning composition for hair comprising at least one cationic starch polymer and at least one additional cationic polymer selected from the ones with monosaccharide units. Conditioning composition of the present invention can be in the form of a shampoo, cleansing-conditioning composition, or in the form of a conditioner used after washing hair with cleansing compositions.

Conditioning compositions for hair have been known for ages. Various types of conditioners are available on the market and new ones are being introduced almost every day. Although this extremely developed conditioner market for hair, there is still need for improvements.

Among important properties of hair, volume, body and shine are the ones addressed very often. On the other hand, it has been observed that smooth feeling of hair is very much wished by the users and at the same time improved looseness and bounce are preferred properties.

It has been observed that know monosaccharide derived cationic polymers make hair satisfactorily smooth but hair treated with such composition often lack looseness and bounce.

It has been surprisingly found out that combination of starch derived cationic polymer, especially oxidized starch derived cationic polymer and another monosaccharide derived cationic polymer makes hair smooth and at the same time improved looseness and bounce. Such effects are especially pronounced when hair is damaged and excellently improved properties were observed with fine hair. Since hair becomes smooth, hair appears with enhanced shine and at the same time volume and body are as well improved because of improved looseness and bounce.

Therefore, first objective of the present invention is to provide an aqueous conditioning composition for hair which conditions hair satisfactorily and especially in terms of improved smoothness, looseness and bounce. Furthermore, other properties of hair are maintained or improved as well such as shine, volume, body and softness.

It has surprisingly been found out that aqueous composition comprising at least one starch derived cationic polymer and at least one additional monosaccharide derived cationic polymer conditions hair satisfactorily in terms of improved smoothness, looseness and bounce.

Accordingly the first object of the present invention is aqueous conditioning composition for hair comprising at least one starch derived cationic polymer and at least one monosaccharide derived cationic polymer.

Further object of the present invention is the use of the compositions of the present invention to condition hair especially fine hair and especially damaged hair especially in terms of smoothness, looseness and bounce.

Still further object of the present invention is the method of conditioning hair wherein hair is treated with at least one composition of the present invention and optionally rinsed off from hair after a processing time of 1 to 30 min.

It has also been observed during the course of tests that the effects are more pronounced when both cleansing and conditioning compositions and conditioning composition without any cleansing effect comprise at least one starch derived cationic polymer and at least one monosaccharide derived cationic polymer. Thus, further object of the present invention is a process for cleansing and conditioning hair wherein a cleansing and conditioning composition is applied onto hair and after rinsing off a conditioning composition without any cleansing effect is applied and optionally rinsed off from hair wherein both compositions comprise at least one starch derived cationic polymer and at least one additional monosaccharide derived cationic polymer.

Further, according to the above process, the object of the present invention is kit for cleansing and conditioning hair comprising at least two compositions where at least one the compositions comprises at least one starch derived cationic polymer and at least one monosaccharide derived cationic polymer.

Within the whole content of the present description it must be understood that the second polymer, monosaccharide derived cationic polymer, does not include any starch derived cationic polymers. Furthermore, with the term "starch derived" in the claims it is meant that the polymer includes a starch backbone and with the term "monosaccharide derived" it is meant that the polymer includes monosaccharide unit in its backbone.

Compositions of the present invention comprises at least one starch derived cationic polymer. Preferred is a cationic oxidized starch polymer known with it CTFA/INCI name hydroxypropyl Oxidized Starch PG-Trimonium chloride available from Graefe Chemie GmbH under the trade name Amylomer.

Concentration of starch derived cationic polymer in the compositions is in the range of 0.01 to 5%, preferably 0.02 to 4%, more preferably 0.05 to 3% and most preferably 0.1 to 2.5% by weight calculated to total composition.

Composition of the present invention comprises at least one additional monosaccharide derived cationic polymer.

With the term monosaccharaide derived cationic polymer, it is meant that the cationic polymer is derived from polymers of monosaccharide. Preferred are especially the ones derived from natural monosaccaharide polymers. Suitable ones are cellulose, guar, chitosan and xanthan derived cationic polymers.

It has further been found out that especially those of cationic cellulose type polymers known as Polymer JR type from Amerchol such as Polyquaternium 10, polyquaternium 4 and polyquaternium 24 or cationic galactomannans such as cationic guar gum known with trade name Jaguar from Rhône-Poulenc which are chemically for example Guar hydroxypropyl trimonium chloride and hydroxypropyl Guar hydroxypropyl trimonium chloride and cationic tara gum an its derivatives known with INCI name Caesalpinia spinosa hydroxypropyltrimonium chloride, are preferred ones.

The most preferred cationic polymers are those of guar derivatives such as Guar hydroxypropyl trimonium chloride and hydroxypropyl Guar hydroxypropyl trimonium chloride.

Concentration of at least one monosaccharide derived cationic polymer is in the range of 0.01 to 5%, preferably 0.02 to 4%, more preferably 0.05 to 3% and most preferably 0.1 to 2.5% by weight calculated to total composition.

It has also been found out that the weight ratio of the two cationic polymers, at least one starch derived cationic polymer to monosaccharaide derived cationic polymer is preferably in the range of 5:1 to 1:5, more preferably 2:1 to 1:2 and most preferably 1:1.

The compositions of the present invention can be either a conditioning-cleansing composition-shampoo-or a conditioning composition typically used after use of cleansing compositions Compositions of the present invention, the ones without cleansing effect, are suitable for either rinse off or leave in applications. Further object of the present invention is a process for conditioning hair wherein a composition according to present invention is applied onto hair and optionally rinsed off.

The composition of the present invention comprises additional hair-conditioning agents in any type of composition. Conditioning agents can be selected from oily substances, non-ionic substances, cationic amphiphilic ingredients, cationic polymers or their mixtures.

Oily substances are selected from such as natural oils such as olive oil, almond oil, avocado oil, wheatgerm oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Oily substances may also be selected from silicones. Accordingly, compositions of the present invention comprise additionally at least one silicone compound. In principal any silicone compound is suitable for the purposes of the present invention. However, silicone compound is preferably selected from dimethicones, dimethiconols, polydimethylsiloxanes, arylated silicones, cyclic silicones, silicone surfactants and aminated silicones.

Silicone compound is preferably oil and selected from volatile and non-volatile ones. Among silicone oils non-limiting suitable ones include dimethicone, dimethiconol, polydimethylsiloxane which are available from various suppliers such as Dow Corning.

Further suitable additional silicone compounds are arylated silicones. Non-limiting suitable examples are phenyl methicone, phenyl trimethicone, diphenyl dimethicone, diphenylsiloxy phenyl trimethicone, tetramethyl tetraphenyl trisiloxane, triphenyl trimethicone, and trimethyl pentaphenyl trisiloxane.

Further suitable volatile silicones are cyclic silicones as volatile silicones according to general formula

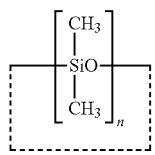

where n is a number between 3 and 7. Examples are cyclomethicone, cycloheptasiloxane, cyclohexasiloxane, cyclopentasiloxane, cyclotetrasiloxane, and cyclotrisiloxane.

Further suitable ones are silicone surfactants which can be selected PEG/PPG-3/10 Dimethicone, PEG/PPG-4/12 Dimethicone, PEG/PPG-6/4 Dimethicone, PEG/PPG-6/11 Dimethicone, PEG/PPG-8/14 Dimethicone, PEG/PPG-8/26 Dimethicone, PEG/PPG-10/2 Dimethicone, PEG/PPG-12/16 Dimethicone, PEG/PPG-12/18 Dimethicone, PEG/PPG-14/4 Dimethicone, PEG/PPG-15/5 Dimethicone, PEG/PPG-15/15 Dimethicone, PEG/PPG-16/2 Dimethicone, PEG/PPG-16/8 Dimethicone, PEG/PPG-17/18 Dimethicone, PEG/PPG-18/6Dimethicone, PEG/PPG-18/12 Dimethicone, PEG/PPG-18/18 Dimethicone, PEG/PPG-19/19 Dimethicone, PEG/PPG-20/6 Dimethicone, PEG/PPG-20/15 Dimethicone, PEG/PPG-20/20 Dimethicone, PEG/PPG-20/23 Dimethicone, PEG/PPG-20/29 Dimethicone, PEG/PPG-22/23 Dimethicone, PEG/PPG-22/24 Dimethicone, PEG/PPG-23/6 Dimethicone, PEG/PPG-25/25 Dimethicone, PEG/PPG-27/27 Dimethicone, and PEG/PPG-30/10 Dimethicone and mixture thereof.

Further suitable ones are aminated silicones carrying at least one amine group in its molecule which may be primary, secondary, tertiary or quaternary amine. Among suitable ones the compounds known with their INCI names Amodimethicone and its derivatives are suitable. Mention should also be made to the ones such as quaternium 80, silicone quaternium-1, silicone quaternium-2, silicone quaternium-2 panthenol succinate, silicone quaternium-3, silicone quaternium-4, silicone quaternium-5, silicone quaternium-6, silicone quaternium-7, silicone quaternium-8, silicone quaternium-9, silicone quaternium-10, silicone quaternium-11, silicone quaternium-12, silicone quaternium-15, silicone quaternium-16, silicone quaternium-16/Glycidoxy Dimethicone Crosspolymer, silicone quaternium-17, silicone quaternium-18, silicone quaternium-20 and silicone quaternium-21. Further suitable ones are according to the general structure Suitable alkoxylated and hydroxylated amino silicones are according to general formula

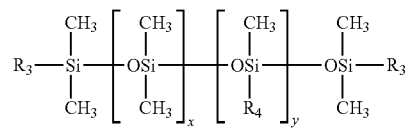

wherein $R_3$ is hydroxyl or $OR_5$ wherein $R_5$ is a $C_1$ to $C_4$ alkyl group, $R_4$ is a group with structure according to general formula

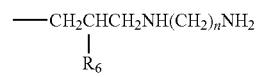

wherein $R_6$ is a $C_1$ to $C_4$ alkyl and n is a 1 to 4, with the condition that $R_3$ is partly hydroxyl group and partly $OR_5$ group and $R_3$ is never only hydroxyl group and only $OR_5$ group. A non-limiting example of the above formula is Bis-hydroxy/methoxy amodimethicone.

In the preferred from of the present invention compositions comprise at least one aminated silicone and at least one other silicone compound as the additional silicone compound which is different from the one with multiple quaternary ammonium groups in its molecule.

Concentration of at least one silicone compound is in the range of 0.01 to 10%, preferably 0.02 to 7.5%, more preferably 0.05 to 5% and most preferably 0.1 to 3% by weight calculated to total composition. It should be noted that the compositions can comprise more than one additional silicone compound and the concentration ranges given here refer to the total concentration.

Concentration of one or more oily substances is in the range of 0.01 to 10%, preferably 0.05 to 7.5%, more preferably 0.1 to 5 and most preferably 0.1 to 3% by weight calculated to total composition. The concentrations referred here are total concentration of all oily substances may be present in the composition.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $R_3CO(OCH_2CH_2)_nOH$ or $R_3CO(OCH_2CH_2)_nOOCR_4$ where $R_3$ and $R_4$ are independent from each other saturated, unsaturated or branched or non-branched alkyl chain with 7 to 21 C atoms and n is typically 2-100.

Concentration of one or more non-ionic conditioning agents is in the range of 0.01 to 10%, preferably 0.05 to 7.5%, more preferably 0.1 to 5 and most preferably 0.1 to 3% by weight calculated to total composition. The concentrations referred here are total concentration of all non-ionic conditioning agents may be present in the composition.

Conditioning compositions may further comprise cationic polymers different from the ones already specified as additional conditioning agent. Suitable are those of best known with their CTFA category name Polyquaternium. Typical examples of those are Polyquaternium 1, Polyquaternium 2, Polyquaternium 5, Polyquaternium 6, Polyquaternium 7, Polyquaternium 8, Polyquaternium 9, Polyquaternium 11, Polyquaternium 12, Polyquaternium 13, Polyquaternium 14, Polyquaternium 15, Polyquaternium 16, Polyquaternium 17, Polyquaternium 18, Polyquaternium 19, Polyquaternium 20, Polyquaternium 22, Polyquaternium 27, Polyquaternium 28, Polyquaternium 29, Polyquaternium 30, Polyquaternium 31, Polyquaternium 32, Polyquaternium 33, Polyquaternium 34, Polyquaternium 35 and Polyquaternium 36, Polyquaternium-37, Polyquaternium 39, Polyquaternium 42, Polyquaternium 43, Polyquaternium 44, Polyquaternium 45, Polyquaternium 46, Polyquaternium 47, Polyquaternium 48, Polyquaternium-49, Polyquaternium 50, Polyquaternium 51, Polyquaternium 52, Polyquaternium 53, Polyquaternium 54, Polyquaternium 55, Polyquaternium 56, Polyquaternium 57, Polyquaternium 58, Polyquaternium 59, Polyquaternium 60, Polyquaternium 61, Polyquaternium 62, Polyquaternium 63, Polyquaternium 64, Polyquaternium 65, Polyquaternium 66, Polyquaternium 67, Polyquaternium 68, Polyquaternium 69, Polyquaternium-70, Polyquaternium 71, Polyquaternium 72, Polyquaternium 73, Polyquaternium 74, Polyquaternium 75, Polyquaternium 76, Polyquaternium 77, Polyquaternium 78, Polyquaternium-79, Polyquaternium 80, Polyquaternium 81, Polyquaternium 82, Polyquaternium 83, Polyquaternium 84, Polyquaternium 85, Polyquaternium 86 and Polyquaternium 87.

Conditioning compositions of the present invention can comprise additionally one or more cationic surfactant(s) as conditioner presented with the general formula

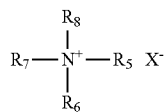

where $R_5$ is a saturated or unsaturated, branched or non-branched alkyl chain with 8-24 C atoms or $R_9CONH(CH_2)_n$ where $R_9$ is saturated or unsaturated, branched or non-branched alkyl chain with 7-21 C atoms and n has value of 1-4, or $R_{10}COO(CH_2)_n$ where $R_{10}$ is saturated or unsaturated, branched or non-branched alkyl chain with 7-21 C atoms and n has value of 1-4, and $R_6$ is hydrogen or unsaturated or saturated, branched or non-branched alkyl chain with 1-24 C atoms or $R_9CONH(CH_2)_n$ or $R_{10}COO(CH_2)_n$ where $R_9$, $R_{10}$ and n are same as above.

$R_7$ and $R_8$ are hydrogen or lower alkyl chain with 1 to 4 carbon atoms which may be substituted with one or more hydroxyl group, and X is anion such as chloride, bromide, methosulfate.

Typical examples of those ingredients are cetyltrimethyl ammonium chloride, steartrimonium chloride, behentrimonium chloride, stearamidopropyl trimonuim chloride, dioleoylethyl dimethyl ammonium methosulfate, dioleoylethyl hydroxyethylmonium methosulfate.

Amido amines may as well be used as a conditioning cationic surfactant in the compositions of the present invention. Typical non-limiting example is stearamidopropyl dimethyl amine known with a trade name Tego Amid S18 from Degussa and Lexamine S13 from Inolex.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, and cationic surfactants is in the range of 0.01-10% by weight, preferably 0.01-7.5% by weight, more preferably 0.05-5% and most preferably 0.1-3% by weight calculated to the total composition. It should be noted that especially non-cleansing conditioning type of the products contain higher concentrations of the above mentioned concentrations of the cationic surfactants which at the same time if desired can be emulsifying agent. In cleansing and conditioning type of preparations, concentration of cationic surfactants is lower.

Conditioning composition of the present invention comprises at least one glyceryl ether of the following formula

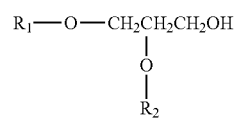

wherein $R_1$ is straight or branched, saturated or unsaturated alkyl chain with 4 to 24 C atoms, preferably 4 to 18 and more preferably 4 to 12 C atoms and $R_2$ is H, or straight or branched, saturated or unsaturated alkyl chain with 4 to 24 C atoms, 4 to 18 and more preferably 4 to 12 C atoms and most preferably $R_5$ is H, at a concentration of 0.1 to 10%, preferably 0.1 to 5% and more preferably 0.25 to 3% and most preferably 0.5 to 2.5% by weight calculated to total composition.

Suitable unlimited examples are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether, glyceryl lauryl ether, glyceryl myristyl ether, glyceryl palmityl ether, glyceryl stearyl ether and glyceryl behenyl ether and their mixtures. Most preferred are glyceryl butyl ether, glyceryl isobutyl ether, glyceryl tert-butyl ether, glyceryl pentyl ether, glyceryl isopentyl ether, glyceryl hexyl ether, glyceryl isohexyl ether, glyceryl heptyl ether, glyceryl octyl ether, glyceryl ethylhexyl ether, glyceryl nonyl ether, glyceryl decyl ether, glyceryl isodecyl ether are glyceryl lauryl ether, and their mixtures.

It should be noted that within the disclosure of the present description, gylceryl decyl ether is used as synonym of decyl glycerine. For the other compounds in the above paragraph the same is valid.

Composition of the present invention can preferably comprise at least one polyphenol. With the word polyphenol it is meant that an organic molecule with at least 2 hydroxyl groups in its molecule.

In the preferred from of the invention, at least one polyphenol or mixture of polyhenols is included into compositions of the present invention from a natural plant extract. In principal any natural plant extract rich of polyphenols is suitable within the meaning of the present invention. Within the meaning of the present invention the extracts are liquid extracts and prepared by mixing plant parts such as leaves, fruits, blossoms and roots with a solvent such as water, alcohol, propyleneglycol or mixture of more than one solvent and incubating for certain period of time and filtrating the undissolved plant parts. Suitable aqueous (e.g. steam-distilled) alcoholic or hydro-alcoholic plant extracts known per se are in particular aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, the various "Extrapon®" products, "Herbasol®", "Sedaplant®" and "Hexaplant®". Extracts and the preparation thereof are also described in "Hagers Handbuch der pharmazeutischen Praxis", 4$^{th}$ Ed. Preferred plant extracts are prepared from *Vitis vinifera, Malus domestica, Camelia sinensis, Juglans regia Ribes Uva-Crispa, Ribes nigrum, Ribes rubrum* and *Punica granatum*. The above mentioned extracts may also be available in the powder form and such are also suitable within the meaning of the present invention.

The polyphenol comprising extracts are included into the compositions of the present invention at a concentration of 0.001 to 10%, preferably 0.005 to 7.5%, more preferably 0.01 to 5% and most preferably 0.05 to 2.5% by weight, calculated to total composition based on dry matter of the extract.

In another preferred form of the invention, conditioning composition comprises one or more organic solvent such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzylalcohol and polypropylene glycols. Concentration of organic solvents should not exceed 10% by weight, preferably in the range of 0.1 to 7.5%, more preferably 0.1 to 5% by weight and most preferably 0.1 to 3% by weight calculated to total composition.

Further in preferred embodiment of the present invention, compositions comprise at least one UV filter and at least one ubichinone of the following formula

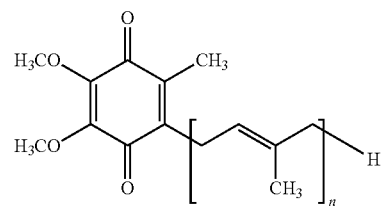

where n is a number between 1 and 10. It should be noted that the compositions of the present invention can certainly comprise more than one ubichinone. Preferred ubichinones are the ones where n is a number between 6 and 10 and especially preferred is Ubichinone 50 where n is 10, also known as Coenzyme Q10. Concentration ubichinone of the above formula in the compositions is from 0.0001 to 1%, preferably from 0.0002 to 0.75%, more preferably from 0.0002 to 0.5% and most preferably from 0.0005 to 0.5% by weight, calculated to total composition.

Compositions of the present invention preferably comprise at least one UV filter. Principally any substance known as UV filter is suitable for the compositions of the present invention. Non-limiting examples are 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2.4-dihydroxybenzophenone, 2.2'.4.4'-tetrahydroxy-benzophenone, 2-hydroxy-4-methoxybenzophenone and its 5-sulfonic acid or the sodium salt thereof, 2.2'-dihydroxy-4.4'-dimethoxybenzophenone, 2-hydroxy-5-chlorobenzophenone, 2.2'-dihydroxy-4-methoxybenzophenone, 2.2'-dihydroxy-4.4'-dimethoxy-5.5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof, 3-(4'-methyl benzylidene)-DL-campher, and/or polysilicone-15. Above mentioned UV filters are those oil and water soluble ones for the purpose of protecting hair colour. In other words, anionic and nonionic, oily, UV filters are suitably used in the compositions of the present invention. In the preferred from of the invention the compositions comprise at least one water soluble UV filter and at least one oil soluble one. Further preferred that both UV filters are present at a weight ratio in the range of oil soluble to water soluble UV filter 1:10 to 10:1, preferably 1:5 to 5:1, more preferably 1:3 to 3:1 and most preferably 1:1 in the compositions of the present invention.

The amount of the UV-absorber as a total ranges typically from about 0.01% to 5%, preferably 0.05 to 3%, more preferably from 0.05% to 2.5% and most preferably from 0.1% to 2% by weight, calculated to the total composition.

Further in preferred embodiment of the present invention, compositions comprise at least one direct dye. Suitable direct dyes are of cationic, anionic and neutral nitro dyes. It should be noted that they can also be used in combination with each other. In other words a composition according to present invention can comprise an anionic and a cationic dye as well as an anionic and a nitro dye or a cationic and a nitro dye. Certainly the combination of all three dyestuffs is also possible.

Any cationic direct dye is in principal suitable for the compositions. Examples are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Orange 31, Basic Red 2, Basic Red 12 Basic Red 22, Basic Red 51, Basic Red 76, Basic Violet 1, Basic Violet 2, Basic Violet 3, Basic Violet 10, Basic Violet 14, Basic Yellow 57 and Basic Yellow 87.

Any anionic dye is in principal suitable for the compositions. Suitable examples are such as Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium.

Among those, the preferred anionic dyestuffs are Acid Red 52, Acid Violet 2, Acid Red 33, Acid Orange 4, Acid Red 27 and Acid Yellow 10 and their salts. The most preferred anionic dyes are Acid Red 52, Acid Violet 2, Acid Red 33, Acid Orange 4 and Acid Yellow 10, and their salts Neutral dyes, so called nitro dyes for shading purposes are also optionally contained in the compositions. Suitable ones are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid.

Concentration of one or more direct dyes in total is in the range of 0.001 to 5% by weight, preferably 0.01 to 4% more preferably 0.05 to 3% and most preferably 0.1 to 2.5% by weight calculated to total composition.

Compositions of the present invention comprise additionally at least one fatty alcohol of the following formula

$R_{15}$—OH where $R_{15}$ is a saturated or unsaturated, branched or non-branched fatty acyl chain with 8-24 C atoms. Concentration of fatty alcohols is usually less than 20%, preferably less than 15% by weight calculated to total composition. Typical examples to the most useful fatty alcohols are myristyl alcohol, palmityl alcohol, cetyl alcohol, stearyl alcohol, behenyl alcohol and their mixtures. As a mixed fatty alcohol the mostly used one is the cetearyl alcohol as well preferred in the compositions of the present invention.

Conditioning compositions of the present invention can be a cleansing composition (cleansing-conditioning composition). Cleansing conditioning compositions of the present invention comprise at least one surfactant selected from anionic, non-ionic and/or amphoteric or zwitterionic surfactants at a concentration range of 5 to 50%, preferably 5 to 40% and more preferably 5 to 30%, and most preferably 5 to 25% by weight, calculated to the total composition.

In an embodiment of the present invention cleansing conditioning composition of the present invention, comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, by weight, calculated to the total composition.

These are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

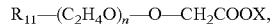
$R_{11}$—$(C_2H_4O)_n$—O—$CH_2COOX$, wherein $R_{11}$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

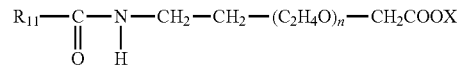

$$R_{11}-\underset{\underset{O}{\|}}{C}-\underset{\underset{H}{|}}{N}-CH_2-CH_2-(C_2H_4O)_n-CH_2COOX$$

wherein $R_{11}$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

An overview of the anionic surfactants used in liquid body cleansing compositions can furthermore be found in the monography of K. Schrader and A. Domsch, "Cosmetology—Theory and Practice", 2005, Verlag für chemische Industrie, Augsburg—Germany, pp. II-8-II-19.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Further surfactants in the conditioning-cleansing compositions according to the invention are nonionic surfactants, preferably in admixture with anionic surfactants.

These are described in Schrader, I. c., on pages 600-601 and pp. 694-695. Especially suited are alkyl polyglucosides of the general formula

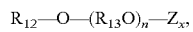

wherein $R_{12}$ is an alkyl group with 8 to 18 carbon atoms, $R_{13}$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components are, for example, long-chain fatty acid mono- and dialkanolamides, such as coco fatty acid monoethanolamide and myristic fatty acid monoethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides which may be present in an amount from 0.25% to 5% by weight, calculated to the total composition.

Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl aminoxides, $C_{12}$-$C_{18}$-alkyl di(hydroxyethyl) or (hydroxypropyl) aminoxides, or also aminoxides with ethyleneoxide and/or propyleneoxide groups in the alkyl chain. Such aminoxides are on the market, for example, under the trade names "Ammonyx®", "Aromox®" or "Genaminox®".

Further nonionic surfactants useful in the cleansing conditioning compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

As further surfactant component, the cleansing conditioning compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

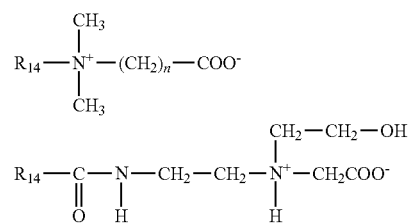

wherein $R_{14}$ is a $C_8$-$C_{18}$-alkyl group and n is 1 to 3;
sulfobetaines of the structure

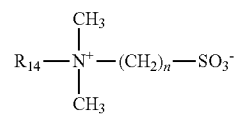

wherein $R_{14}$ and n are same as above;
and amidoalkyl betaines of the structure

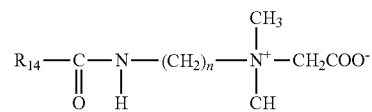

wherein $R_{14}$ and n are same as above.

Solubilizers may be added to the compositions, in particular cleansing compositions, especially when oily substances are chosen as conditioning agents and fragrance oils with highly lipophilic properties. Typical solubilizers may be hydrogenated castor oil known with the trade mark Cremophor RO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

Conditioning and cleansing composition of the present invention can be transparent as well as pearly. Transparency of the composition is judged by naked eye in a transparent shampoo bottle with a thickness not more than 5 cm. In the case a transparent appearance is wished, the following ingredients are not essential. However, pearl-shiny appearance is achieved with those dispersed in cleansing color-enhancing compositions in crystalline form, i.e. so called pearl-shine or pearlizing agents. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kind of mixtures is available commercially.

Hair cleansing conditioning compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbondioxide, dimethylether and alkanes such as butane propane or their mixtures.

Conditioning compositions of the present invention can be in the form of emulsions, solutions, gels and dispersions. In the case that solutions and/or gels forms are preferred the appearance can be either with a transparent or opaque. As a product form, foam is as well suited when packed into a pressurized can or delivered through a pump-foamer (non-aerosol). In the case that an aerosol foam preparation is preferred, propellant gas must be added to the formulation. The suitable propellant gasses are carbondioxide, dimethylether and alkanes such as butane, propane, isobutane or their mixtures.

Conditioning compositions of the present invention can comprise moisturizers, chelating agents, preservatives and fragrance. The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are selected from polycarboxy acids. The preferred one is ethylene diamine tetraacetic acid, EDTA. Typical useful concentration range for sequestering agents is of 0.01-2.5% by weight calculated to the total composition.

The pH of the compositions according to the present invention is suitably between 2 and 8 and preferably in the range of 2.5 to 6.5, more preferably 3 to 5.5 and most preferably 3.5 to 5.

In principal pH of the compositions can be adjusted with any organic and/or inorganic acids or their mixture. Some of them to mention are phosphoric acid, hydrochloric acid as the inorganic ones and to the organic acids the well known citric acid and lactic acid, glycolic acid, hydroxyacrylic acid, glyceric acid, malic acid and tartaric acid and of the dicarboxylic acids are malonic acid, succinic acid, glutaric acid, adipic acid, maleic acid, fumaric acid and phtalic acid. It has further been observed that improved conditioning and brightening performance was observed when compositions comprise at the same time at least one hydroxycarboxylic and/or dicarboxylic acids.

The viscosity of the conditioning shampoo compositions according to the invention is in the range of 500 and about 20,000 mPa·s at 20° C., preferably 1,000 to 10,000, in particular 1,500 to 8,000 mPa·s at 20° C., measured with Höppler viscosimeter.

Viscosity of shampoo compositions can be adjusted with known viscosity enhancers. The preferred ones are glyceryl laurate, PEG-55 propyleneglycol oleate and PEG-18 glyceryl oleate/cocoate known with the trade names Antil® 141 and 171, respectively and PEG-160 sorbitan triisostearate known with a trade name Rheodol®. It should be noted that in the case that a composition are delivered in the form of a foam from a pump-foamer and/or aerosol can, those compositions should not be thickened and have a viscosity value not more than 500 mPa·s, more preferably 250 mPa·s measured as mentioned above at room temperature.

Viscosity of the non-cleansing conditioning composition should not be more than 50,000 mPa·s at 20° C. measured with Brookfield Rheometer at a shear rate of 10 sec$^{-1}$.

The following examples are to illustrate the invention, but not to limit. The compositions according to the invention are prepared by mixing the individual components in water, whereby it is also possible to use pre-mixtures of various ingredients.

EXAMPLE 1

| | |
|---|---|
| Sodium lauryl ether sulfate | 11.0 (% by wt.) |
| Coco glucoside | 4.0 |
| Cocoamidopropyl betaine | 1.5 |
| Guar hydroxyprolytrimonium chloride | 0.5 |
| Hydroxypropyl oxidized Starch PG trimonium chloride | 0.5 |
| Sodium chloride | 1.0 |
| Citric acid | q.s. pH 5.5 |
| Perfume, preservative | q.s |
| Water | q.s. to 100.0 |

Damaged hair washed with the above shampoo composition felt smooth, lose and bouncy.

In order to show the synergistic effect of the two cationic polymers, comparative compositions were produced comprising only one of the cationic polymers, i.e. comprising only Guar hydroxyprolytrimonium chloride at a concentration of 1.0% by weight (Composition B) and comprising only Hydroxypropyl oxidized Starch PG trimonium chloride at a concentration of 1.0% by weight (Composition C). The three smapoo compositions were tested one by one with 10 volunteers and evaluated after drying hair by 3 hair dressers within a range of marks from 1 (not appreciated) to 5 (very much appreciated). The following results were obtained:

| Hair property | Example 1 | Composition B | Composition C |
|---|---|---|---|
| Smoothness | 4.8 | 4.7 | 3.1 |
| Loseness | 4.6 | 3.1 | 4.2 |
| Bounce | 4.7 | 3.2 | 4.1 |
| Shine | 4.5 | 4.5 | 3.8 |
| Softness | 4.8 | 4.2 | 3.9 |
| Volume | 4.3 | 3.1 | 4.3 |
| Body | 4.3 | 4.2 | 3.1 |

From the above results it is clear that the combination of the two polymers deliver advantageous properties to hair. Such effect is not observed with compositions comprising only one of the two polymers, so that the effect is result of the synergistic interaction of the two polymers.

Similar results are observed with the following shampoo compositions.

EXAMPLE 2

| | |
|---|---|
| Sodium lauryl ether carboxylate (10EO) | 5.0 (% by wt.) |
| Coco glucoside | 5.0 |
| Cocoamidopropyl betaine | 5.0 |
| Sodium lauroyl glutamate | 2.5 |
| Polyquaternium-10 | 0.5 |
| Hydroxypropyl oxidized Starch PG trimonium chloride | 0.5 |
| PEG-60-hydrogenated castor oil | 0.5 |
| PEG-18 Glyceryl cocoate/oleate | 1.0 |
| Camelia sinesis (dry matter) | 0.08 |
| Ubichinone | 0.08 |
| Lactic acid | q.s. pH 5.0 |
| Perfume, preservative | q.s. |
| Water | q.s. to 100 |

Further, into the above shampoo composition 0.1% by weight Basic Red 51, a cationic direct dye, was added. It was observed that hair washed with this shampoo had excellent red shimmer in addition to the smooth, lose and bouncy feeling.

EXAMPLE 3

| | |
|---|---|
| Coco glucoside | 8.0 |
| Cocoamidopropyl betaine | 8.0 |
| Laureth-16 | 2.0 |
| Guar hydroxyprolytrimonium chloride | 0.5 |
| Hydroxypropyl oxidized Starch PG trimonium chloride | 0.5 |
| Benzophenone-3 | 0.2 |
| Dimethicone | 0.8 |
| PEG-3 distearate | 0.8 |
| Coenzyme Q10 | 0.1 |
| Ethyl hexyl methoxy cinnamate | 0.3 |
| PEG-18 Glyceryl cocoate/oleate | 0.80 |
| Malus domestica (dry matter) | 0.1 |
| Malic acid | q.s. pH 4.0 |
| Perfume, preservative | q.s. |
| Water | q.s. to 100 |

To the above composition, 0.1% Basic orange 31 and 0.05% Basic red 76 was mixed. Hair washed with this shampoo had excellent warm blond shine, in addition to the smooth, lose and bouncy feeling.

EXAMPLE 4

| | |
|---|---|
| Sodium lauryl ether sulfate | 11.0 (% by wt.) |
| Coco glucoside | 5.0 |
| Cocoamidopropyl betaine | 3.0 |
| Ethylhexyl glycerin | 0.7 |
| Phenyl trimethicone | 0.2 |
| Laureth-16 | 4.0 |
| Guar hydroxyprolytrimonium chloride | 0.5 |
| Hydroxypropyl oxidized Starch PG trimonium chloride | 0.5 |
| Benzophenone-3 | 0.2 |
| Benzylalcohol | 0.5 |
| Silicone quaternium - 22 | 0.4 |
| Ubichinone | 0.05 |
| Vitis vinifera (dry matter) | 0.20 |
| Propylene glycol | 1.0 |
| Lactic acid | q.s. to pH 5.0 |
| Perfume, preservative | q.s. |
| Water | q.s. to 100 |

The above composition is a very low viscosity composition, in any case a viscosity lower than 500 mPa·s measured at ambient temperature and with Höppler viscosimeter, confectioned into a pump-foamer as purchased from the company Air-Spray—Germany and showed excellent brightening and shine effect Similarly and aerosol foam shampoo was prepared by confectioning the above composition at a weight ratio of 90/10-composition/propellant-using propane-butane mixture as a propellant. The foam shampoos so obtained showed excellent cleansing and brightening and shine effects.

Additionally, into the above shampoo 0.05% basic blue 99, and 0.005% basic red 51 was added. Excellent warm silver shine was observed on the washed gray hair. At the same time, excellent anti-yellow effect is observed on the freshly bleached hair.

Furthermore the above cleansing and conditioning composition was added 1% by weight sodium chloride and it became a thickened shampoo without loss of any effects mentioned above.

EXAMPLE 5

| | |
|---|---|
| Sodium lauryl ether sulfate | 11.0 (% by wt.) |
| Coco glucoside | 5.0 |
| Cocoamidopropyl betaine | 3.0 |
| Sodium cocoyl glutamate | 1.0 |
| Laureth-16 | 4.0 |
| Guar hydroxyprolytrimonium chloride | 0.5 |
| Hydroxypropyl oxidized Starch PG trimonium chloride | 0.5 |
| Benzophenone-3 | 0.2 |
| Benzylalcohol | 0.5 |
| Silicone quaternium - 22 | 0.2 |
| Ubichinone | 0.05 |
| PEG-18 Glyceryl cocoate/oleate | 1.1 |
| Amodimethicone | 0.20 |
| Lactic acid | q.s. to pH 5.0 |
| Perfume, preservative | q.s. |
| Water | q.s. to 100 |

Above shampoo delivers excellent conditioning in terms of smoothness, looseness, bounce, shine volume and body to hair.

EXAMPLE 6

| | |
|---|---|
| Cetylstearylalcohol | 5.0 (% by weight) |
| Stearyltrimethylammoniumchlorid | 2.0 |
| Benzylalcohol | 2.5 |
| Guar hydroxyprolytrimonium chloride | 0.5 |
| Hydroxypropyl oxidized Starch PG trimonium chloride | 0.5 |
| Amodimethicone | 0.9 |
| Fragrance, preservative | q.s. |
| Lactic acid | q.s. pH 3.5 |
| Wasser | q.s. to 100 |

Above composition is applied onto shampooed hair and processed for 5 min and rinsed off from hair. It was observed that wet hair is easily combable. In the dry state smoothness, looseness and bounce were observed to be very much improved in addition to combability, manageability, shine, volume and body. The same were found on hair comprising parts damaged with a previous chemical treatment.

Furthermore into the above conditioner composition, hair direct dye Basic red 51 was included. After use on dark blonde hair am excellent red shine was observed on the hair.

EXAMPLE 7

Foam Conditioner

| | |
|---|---|
| Quaternium-80 | 0.2 (Gew.-%) |
| Guar hydroxyprolytrimonium chloride | 0.5 |
| Hydroxypropyl oxidized Starch PG trimonium chloride | 0.5 |
| PEG-60-hydrogenated ricinus oil | 0.5 |
| Silicone quaternium-22 | 0.5 |
| Ethylhexyl glycerin | 1.2 |
| Malus domestica (dry matter) | 0.1 |
| Ubichinone | 0.075 |
| Benzophenone-3 | 0.3 |
| Fragrance, preservative | q.s. |
| Lactic acid | q.s. to pH 4 |
| Wasser | q.s. to 100 | pH of the composition is adjusted to 3.4. The composition is suitable for leave-in and rinse off. In leave-in application, amount used is obviously less than in the case of a rinse of application. The composition is packed into an aerosol can with 90/10 ratio, by weight, liquid composition to propellant. As propellant propane, butane mixture is used.

Into the above composition 0.1% Acid red 52 was added. It was possible to realize red shimmer onto dark blonde hair.

EXAMPLE 8

| | |
|---|---|
| Cetylstearylalcohol | 5.0 (% by weight) |
| Cetrimoniumchloride | 1.0 |
| Panthenol | 0.4 |
| Dimethicone | 0.75 |
| Hydroxypropyl Guar Hydroxypropyltrimonium Chloride | 0.4 |
| Hydroxypropyl oxidized Starch PG trimonium chloride | 0.4 |
| Decyl glycerin | 1.2 |
| Ubichinone | 0.08 |
| Fragrance, preservative | q.s. |
| Citric acid | q.s. to pH 3.0 |
| Wasser | q.s. to 100 |

The above composition can be used as both leave-in and rinse off.

EXAMPLE 9

| | |
|---|---|
| Cetylstearylalcohol | 5.0 (% by weight) |
| Dioleoylethyldimethylammonium ethosulfate | 1.0 |
| Ceteareth 20 | 1.0 |
| Panthenol | 0.4 |
| Dimethicone | 0.75 |
| Hydroxypropyl Guar Hydroxypropyltrimonium Chloride | 1.0 |
| Hydroxypropyl oxidized Starch PG trimonium chloride | 0.5 |
| Ethylhexyl glycerin | 0.8 |
| Fragrance, preservative | q.s. |
| Malic acid | q.s. to pH 3.5 |
| Wasser | ad 100.0 |

The invention claimed is:

1. An aqueous conditioning composition for hair comprising cationic starch consisting of hydroxypropyl oxidized starch PG trimonium chloride and at least one monosaccharide derived cationic polymer selected from cationic polymers of guar, wherein the ratio of hydroxypropyl oxidized starch PG trimonium chloride to the at least one monosaccharide derived cationic polymer is in the range of 2:1 to 1:2, wherein the hydroxypropyl oxidized starch PG trimonium chloride is present at a concentration of 0.01 to 5% by weight and the at least one monosaccharide derived cationic polymer is present at a concentration of 0.01 to 5% by weight, all values are calculated to total composition.

2. The composition according to claim 1, wherein the cationic polymers of guar are selected from guar hydroxypropyl trimonium chloride and hydroxypropyl guar hydroxypropyl trimonium chloride.

3. The composition according to claim 2, wherein the hydroxypropyl oxidized starch PG trimonium chloride is present at a concentration of 0.1 to 2.5% by weight and the at least one monosaccharide derived cationic polymer is present at a concentration of 0.1 to 2.5% by weight, all values are calculated to total composition.

4. The composition according to claim 1, wherein the monosaccharide derived cationic polymer is guar hydroxypropyl trimonium chloride.

5. The composition according to claim 1, further comprising at least one additional conditioning agent.

6. The composition according to claim 5, further comprising at least one silicone compound.

7. The composition according to claim 1, wherein the composition is an emulsion and comprises at least one fatty alcohol according to general formula $R_{15}$—OH where $R_{15}$ is a saturated or unsaturated, branched or non-branched fatty acyl chain with 8-24 carbon atoms.

8. The composition according to claim 1, further comprising at least one cationic surfactant.

9. The composition according to claim 1, further comprising at least one direct dye.

10. The composition according to claim 1, further comprising at least one UV filter.

11. The composition according to claim 1, wherein the composition is a cleansing and conditioning composition and further comprises at least one anionic surfactant and at least one non-ionic surfactant and at least one amphoteric or zwitterionic surfactant.

12. The composition according to according to claim 1, wherein the composition has a pH in the range of 2.0 to 8.0.

13. The composition according to claim 12, wherein the composition has a pH in the range of 3.5 to 5.

14. A kit for conditioning hair comprising at least two products wherein at least one of the products comprise the composition according to claim 1.

* * * * *